(12) United States Patent
Jin et al.

(10) Patent No.: US 8,051,994 B2
(45) Date of Patent: Nov. 8, 2011

(54) SAMPLE STORAGE APPARATUS

(75) Inventors: Jae Hwa Jin, Daejeon (KR); Jun Ho Kim, Mokop-si (KR); Min Jun Kim, Daejeon (KR)

(73) Assignee: Korea Institute of Geoscience and Mineral Resources (KR)

( * ) Notice: Subject to any disclaimer, the term of this patent is extended or adjusted under 35 U.S.C. 154(b) by 234 days.

(21) Appl. No.: 12/620,298

(22) Filed: Nov. 17, 2009

(65) Prior Publication Data
US 2011/0089128 A1    Apr. 21, 2011

(30) Foreign Application Priority Data
Oct. 16, 2009 (KR) .................. 10-2009-0098950

(51) Int. Cl.
*A47F 5/00* (2006.01)
(52) U.S. Cl. ............ 211/163; 211/144; 211/131.1; 211/196; 211/205
(58) Field of Classification Search ............ 211/163, 211/70, 78, 95, 115, 166, 131.1, 144, 129.1, 211/77, 53, 55, 58, 196, 133.4, 205, 187, 211/190, 208; 108/147.11, 106, 144.11, 108/146, 147.12
See application file for complete search history.

(56) References Cited

U.S. PATENT DOCUMENTS

| | | | |
|---|---|---|---|
| 4,673,653 A | 6/1987 | Guigan | |
| 5,657,878 A * | 8/1997 | Austin | 211/41.8 |
| 5,984,114 A * | 11/1999 | Frankel | 211/34 |
| 6,241,105 B1 * | 6/2001 | Pomper | 211/85.2 |
| 7,144,610 B1 * | 12/2006 | Estes et al. | 428/19 |
| 7,748,545 B2 * | 7/2010 | Johnson | 211/78 |
| 7,975,643 B1 * | 7/2011 | Johnson | 118/14 |
| 2003/0015486 A1 * | 1/2003 | Chen | 211/70 |
| 2008/0307821 A1 | 12/2008 | Zenobi | |
| 2009/0188272 A1 | 7/2009 | Cloutier et al. | |
| 2009/0255288 A1 | 10/2009 | Jia | |
| 2011/0089128 A1 * | 4/2011 | Jin et al. | 211/163 |

FOREIGN PATENT DOCUMENTS
JP    2002-336321 A    11/2002
KR    10-0788756 B1    12/2007
* cited by examiner

*Primary Examiner* — Jennifer E. Novosad
(74) *Attorney, Agent, or Firm* — Park & Associates IP Law, P.C.

(57) ABSTRACT

Disclosed is a sample storage apparatus in that a multilayered rotary table is formed in a liquid nitrogen vessel, so that a plurality of sample storage boxes is stored in the multilayered rotary table, whereby it can effectively and maximally ensure the space for storing the samples. The sample storage apparatus includes: a rotating axis 100; a rotary table 200 having an upper cylinder portion 210 protruded upward from an upper middle portion thereof and allowing the rotating axis 100 to be inserted therein and a lower cylinder portion 220 protruded downward from a lower middle portion thereof and allowing the rotating axis 100 to be inserted therein; at least one partition member 300 for partitioning off an upper surface of the rotary table 200 formed at the upper surface of the rotary table 200; a fixing member 400 coupled to one side of an outer circumference of the lower cylinder portion 220 through a hinge coupling portion 410 and having a lower portion protruded downward from a lower end of the lower cylinder portion 220 and a slanting portion formed at one side of an upper end thereof so as to form a fixing gap angle 430; and a latching member 500 formed along an outer circumference of the upper cylinder portion 210 and having a plurality of insertion holes 510 for allowing a lower end of the fixing member 400 to be inserted therein.

12 Claims, 8 Drawing Sheets

SAMPLE STORAGE APPARATUS

REFERENCE TO RELATED APPLICATIONS

This application claims the priority benefit of Korean Patent Application No. 10-2009-0098950 filed on Oct. 16, 2009, the entire contents of which are incorporated herein by reference.

FIELD OF THE INVENTION

The present invention relates to a sample storage apparatus. More particularly, the present invention relates to a sample storage apparatus in that a multilayered rotary table is formed in a liquid nitrogen vessel, so that a plurality of sample storage boxes is stored in the multilayered rotary table, whereby it can effectively and maximally ensure the space for storing the samples.

BACKGROUND OF THE INVENTION

Generally, a sample storage apparatus serves to store a liquid oxygen, a liquid nitrogen, an argon, or a carbon dioxide gas and so on.

Especially, the sample storage apparatus serves to store a cord blood, a gene, a cell, a bone marrow, a fertilized egg, a white blood corpuscle, valves of the heart, various microorganisms, etc. for a long time.

Figure 1:
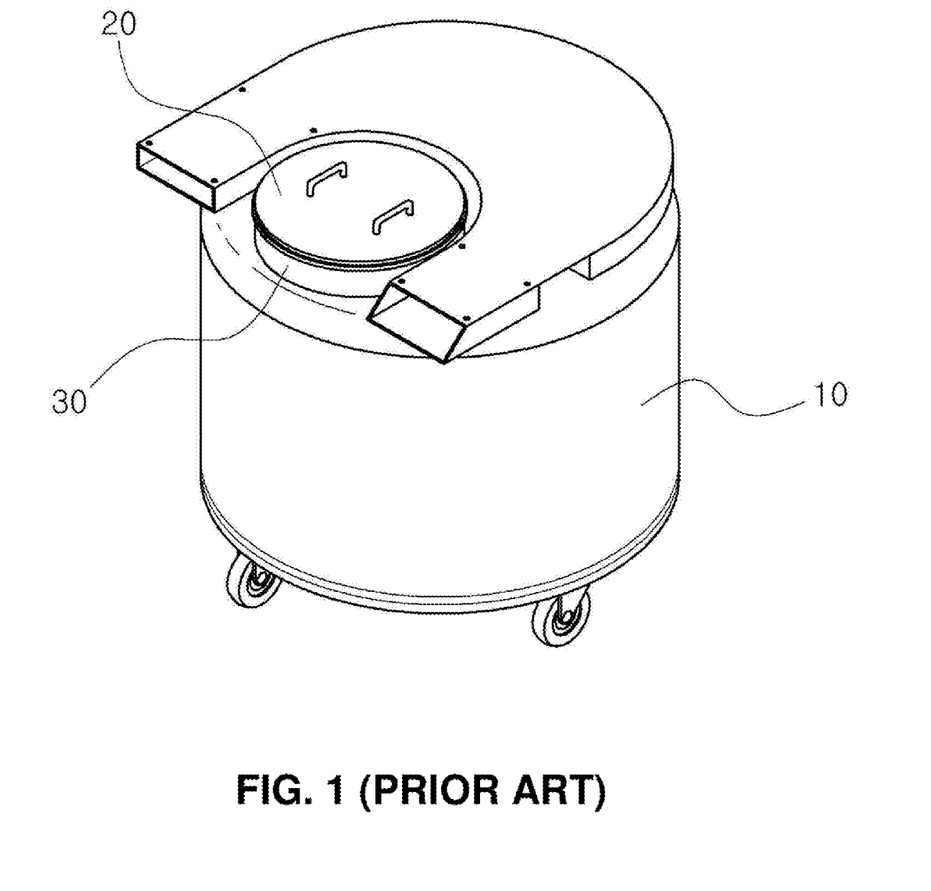
FIG. 1 is a perspective view illustrating a conventional sample storage apparatus.

FIG. 1 is a perspective view illustrating a conventional sample storage apparatus.

As shown in FIG. 1, the conventional sample storage apparatus includes a vessel 10 for storing the liquid nitrogen and so on, a cylindrical entrance 30 for incoming and outgoing the liquid nitrogen, and a cover 20 for covering the cylindrical entrance 30.

However, in the conventional sample storage apparatus, there is a problem in that the entire size of the sample storage apparatus becomes bigger in order to store a plurality of sample storage boxes, thereby increasing manufacturing costs thereof.

SUMMARY OF THE INVENTION

Accordingly, the present invention has been made to solve the above-mentioned problems occurring in the prior art, and an object of the present invention is to provide a sample storage apparatus in that a multilayered rotary table is inserted into a rotating axis, so that a plurality of sample storage boxes is stored in the multilayered rotary table, whereby it can effectively and maximally ensure the space for storing the samples.

Another object of the present invention is to provide a sample storage apparatus in that through holes are formed at a partition member and fixing poles are inserted into the corresponding through holes to fix at least two rotary tables, so that the fixed rotary tables can be rotated at the same time.

Further another object of the present invention is to provide a sample storage apparatus in that viewing holes are formed at the rotary tables and located on an upper portion of the corresponding sample storage boxes, so that the desiring sample storage boxes located at a lower portion of the rotated rotary tables can be easily putted into or drawn out through the viewing holes.

Further another object of the present invention is to provide a sample storage apparatus in that a bearing is formed between upper and lower rotary units or between lower rotary units where the plurality of lower rotary units is formed therein.

In order to accomplish the above objects, according to the present invention, there is provided a sample storage apparatus comprising: a rotating axis 100; a rotary table 200 having an upper cylinder portion 210 protruded upward from an upper middle portion thereof and allowing the rotating axis 100 to be inserted therein and a lower cylinder portion 220 protruded downward from a lower middle portion thereof and allowing the rotating axis 100 to be inserted therein; at least one partition member 300 for partitioning off an upper surface of the rotary table 200 formed at the upper surface of the rotary table 200; a fixing member 400 coupled to one side of an outer circumference of the lower cylinder portion 220 through a hinge coupling portion 410 and having a lower portion protruded downward from a lower end of the lower cylinder portion 220 and a slanting portion formed at one side of an upper end thereof so as to form a fixing gap angle 430; and a latching member 500 formed along an outer circumference of the upper cylinder portion 210 and having a plurality of insertion holes 510 for allowing a lower end of the fixing member 400 to be inserted therein.

In order to accomplish the above objects, according to the present invention, there is provided a sample storage apparatus comprising: a rotating axis 100; a rotary table 200 having an upper cylinder portion 210 protruded upward from an upper middle portion thereof and allowing the rotating axis 100 to be inserted therein and a lower cylinder portion 220 protruded downward from a lower middle portion thereof and allowing the rotating axis 100 to be inserted therein; at least one partition member 300 for partitioning off an upper surface of the rotary table 200 formed at the upper surface of the rotary table 200; a fixing member 400 coupled to one side of an outer circumference of the lower cylinder portion 220 through a hinge coupling portion 410 and having a lower portion protruded downward from a lower end of the lower cylinder portion 220 and a slanting portion formed at one side of an upper end thereof so as to form a fixing gap angle 430; a latching member 500 formed along an outer circumference of the upper cylinder portion 210 and having a plurality of insertion holes 510 for allowing a lower end of the fixing member 400 to be inserted therein; and at least two through holes 310 formed at the partition members 300 in a predetermined distance.

According to the preferred embodiment of the present invention, a plurality of rotary tables is stacked up another through the rotating axis.

According to the preferred embodiment of the present invention, the sample storage apparatus further comprises a bearing 600 having an axis insertion hole for allowing the rotating axis 100 to be inserted therein located on the upper cylinder portion 210.

According to the preferred embodiment of the present invention, the sample storage apparatus further comprises viewing holes formed at least one partition district of the rotary table 200 divided by the partition members.

In order to accomplish the above objects, according to the present invention, there is provided a sample storage apparatus comprising: a rotating axis 100; an upper rotary unit 1000 having a first rotary table 200 having a first upper cylinder portion 210 protruded upward from an upper middle portion thereof and allowing a rotating axis 100 to be inserted therein and a first lower cylinder portion 220 protruded downward from a lower middle portion thereof and allowing the rotating axis 100 to be inserted therein, at least one first partition members 300 for partitioning off an upper surface of the first rotary table 200 formed at the upper surface of the first rotary table 200, and a first fixing member 400 coupled to one side of an outer circumference of the first lower cylinder portion 220 through a first hinge coupling portion 410 and having a lower portion protruded downward from a lower end of the first lower cylinder portion 220 and a first slanting portion 420 formed at one side of an upper end thereof so as to form a first fixing gap angle 430; and a lower rotary unit 2000 located at a lower portion of the upper rotary unit 1000 having a second rotary table 200 having a second upper cylinder portion 210 protruded upward from an upper middle portion thereof and allowing the rotating axis 100 to be inserted therein and a second lower cylinder portion 220 protruded downward from a lower middle portion thereof and allowing the rotating axis 100 to be inserted therein; at least one second partition members 300 for partitioning off an upper surface of the second rotary table 200 formed at the upper surface of the second rotary table 200, a second fixing member 400 coupled to one side of an outer circumference of the second lower cylinder portion 220 through a second hinge coupling portion 410 and having a lower portion protruded downward from a lower end of the second lower cylinder portion 220 and a second slanting portion 420 formed at one side of an upper end thereof so as to form a second fixing gap angle 430, and a latching member 500 formed along an outer circumference of the second upper cylinder portion 210 and having a plurality of second insertion holes 510 for allowing a lower end of the first fixing member 400 of the upper rotary unit 1000 to be inserted into the insertion holes, wherein at least two lower rotary units 2000 are stacked up another.

In order to accomplish the above objects, according to the present invention, there is provided a sample storage apparatus comprising: a rotating axis 100; an upper rotary unit 1000 having a first rotary table 200 having a first upper cylinder portion 210 protruded upward from an upper middle portion thereof and allowing a rotating axis 100 to be inserted therein and a first lower cylinder portion 220 protruded downward from a lower middle portion thereof and allowing the rotating axis 100 to be inserted therein, at least one first partition members 300 for partitioning off an upper surface of the first rotary table 200 formed at the upper surface of the first rotary table 200, and a first fixing member 400 coupled to one side of an outer circumference of the first lower cylinder portion 220 through a first hinge coupling portion 410 and having a lower portion protruded downward from a lower end of the first lower cylinder portion 220 and a first slanting portion 420 formed at one side of an upper end thereof so as to form a first fixing gap angle 430; and a lower rotary unit 2000 located at a lower portion of the upper rotary unit 1000 having a second rotary table 200 having a second upper cylinder portion 210 protruded upward from an upper middle portion thereof and allowing the rotating axis 100 to be inserted therein and a second lower cylinder portion 220 protruded downward from a lower middle portion thereof and allowing the rotating axis 100 to be inserted therein; at least one second partition members 300 for partitioning off an upper surface of the second rotary table 200 formed at the upper surface of the second rotary table 200, a second fixing member 400 coupled to one side of an outer circumference of the second lower cylinder portion 220 through a second hinge coupling portion 410 and having a lower portion protruded downward from a lower end of the second lower cylinder portion 220 and a second slanting portion 420 formed at one side of an upper end thereof so as to form a second fixing gap angle 430, and a latching member 500 formed along an outer circumference of the second upper cylinder portion 210 and having a plurality of second insertion holes 510 for allowing a lower end of the first fixing member 400 of the upper rotary unit 1000 to be inserted into the insertion holes, wherein at least two lower rotary units 2000 are stacked up another, and a bearing 600 having an axis insertion hole for allowing the rotating axis 100 to be inserted therein located on the second upper cylinder portion 210 is formed between the upper and lower rotary units or between the lower rotary units, where the plurality of lower rotary units is formed therein.

According to the preferred embodiment of the present invention, at least two through holes 310 are formed at the first and second partition members 300 in a predetermined distance.

According to the preferred embodiment of the present invention, fixing poles are inserted into any through holes formed at the partition members 300, whereby at least two rotary tables can be fixed.

According to the preferred embodiment of the present invention, an upper rotary table 200 is simultaneously rotated with a lower rotary table 200, when the upper rotary table 200 is rotated in the direction of the fixing gap angle 430.

According to the preferred embodiment of the present invention, where an upper rotary table 200 is rotated in the opposite direction of the fixing gap angle 430, the upper rotary table 200 is not engaged with a lower rotary table 200, whereby the upper rotary table 200 can be freely rotated.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE INVENTION

Hereinafter, the present invention will be described with reference to accompanying drawings.

Figure 2:
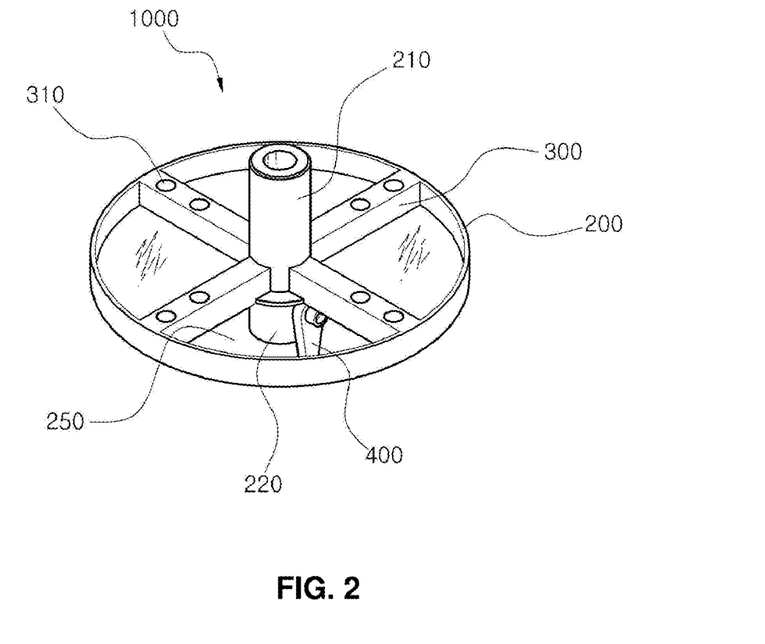
FIG. 2 is a perspective view illustrating an upper rotary unit of a sample storage apparatus according to the present invention.

FIG. 2 is a perspective view illustrating an upper rotary unit of a sample storage apparatus according to the present invention.

As shown in FIG. 2, the upper rotary unit 1000 of the sample storage apparatus according to the present invention basically includes a first rotary table 200 having a first upper cylinder portion 210 protruded upward from an upper middle portion thereof and allowing a rotating axis 100 to be inserted therein and a first lower cylinder portion 220 protruded downward from a lower middle portion thereof and allowing the rotating axis 100 to be inserted therein; at least one first partition members 300 for partitioning off an upper surface of the first rotary table 200 formed at the upper surface of the first rotary table 200; and a first fixing member 400 coupled to one side of an outer circumference of the first lower cylinder portion 220 through a first hinge coupling portion 410 and having a lower portion protruded downward from a lower end of the first lower cylinder portion 220 and a first slanting portion 420 formed at one side of an upper end thereof so as to form a first fixing gap angle 430.

As occasion demands, the upper rotary unit 1000 of the sample storage apparatus according to the present invention further includes a first latching member 500 formed along an outer circumference of the first upper cylinder portion 210 and having a plurality of first insertion holes 510 for allowing a lower end of the first fixing member 400 to be inserted therein.

More concretely, in the first rotary table 200, the first upper cylinder portion 210 is protruded upward from the upper middle portion of the first rotary table 200, thereby allowing the rotating axis 100 to be inserted therein. Also, the first lower cylinder portion 220 is protruded downward from the lower middle portion of the first rotary table 200, thereby allowing the rotating axis 100 to be inserted therein.

Here, where the rotating axis 100 is vertically inserted into an lower rotary unit 2000, viewing holes 250 are formed at least one partition district of the first rotary table 200 divided by the first partition members 300, so that the desiring sample storage boxes 900 seated on the lower rotary unit 2000 can be easily putted into or drawn out through the viewing holes 250.

Figure 3:
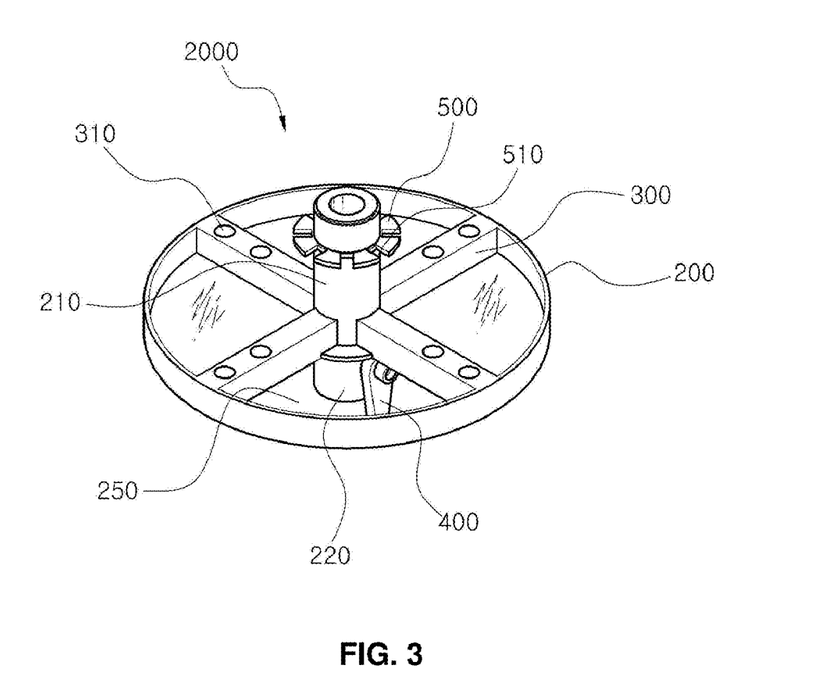
FIG. 3 is a perspective view illustrating a lower rotary unit of the sample storage apparatus according to the present invention.

FIG. 3 is a perspective view illustrating a lower rotary unit of the sample storage apparatus according to the present invention.

As shown in FIG. 3, the lower rotary unit 2000 located at a lower portion of the upper rotary unit 1000 of the sample storage apparatus according to the present invention includes a second rotary table 200 having a second upper cylinder portion 210 protruded upward from an upper middle portion thereof and allowing the rotating axis 100 to be inserted therein and a second lower cylinder portion 220 protruded downward from a lower middle portion thereof and allowing the rotating axis 100 to be inserted therein; at least one second partition members 300 for partitioning off an upper surface of the second rotary table 200 formed at the upper surface of the second rotary table 200; a second fixing member 400 coupled to one side of an outer circumference of the second lower cylinder portion 220 through a second hinge coupling portion 410 and having a lower portion protruded downward from a lower end of the second lower cylinder portion 220 and a second slanting portion 420 formed at one side of an upper end thereof so as to form a second fixing gap angle 430; and a second latching member 500 formed along an outer circumference of the second upper cylinder portion 210 and having a plurality of second insertion holes 510 for allowing a lower end of the first fixing member 400 of the upper rotary unit 1000 to be inserted therein.

Here, a bearing 600 having an axis insertion hole for allowing the rotating axis 100 to be inserted therein is located on the first and the second upper cylinder portion 210. That is, the bearing 600 is formed between upper and lower rotary units 1000 and 2000.

Figure 4:
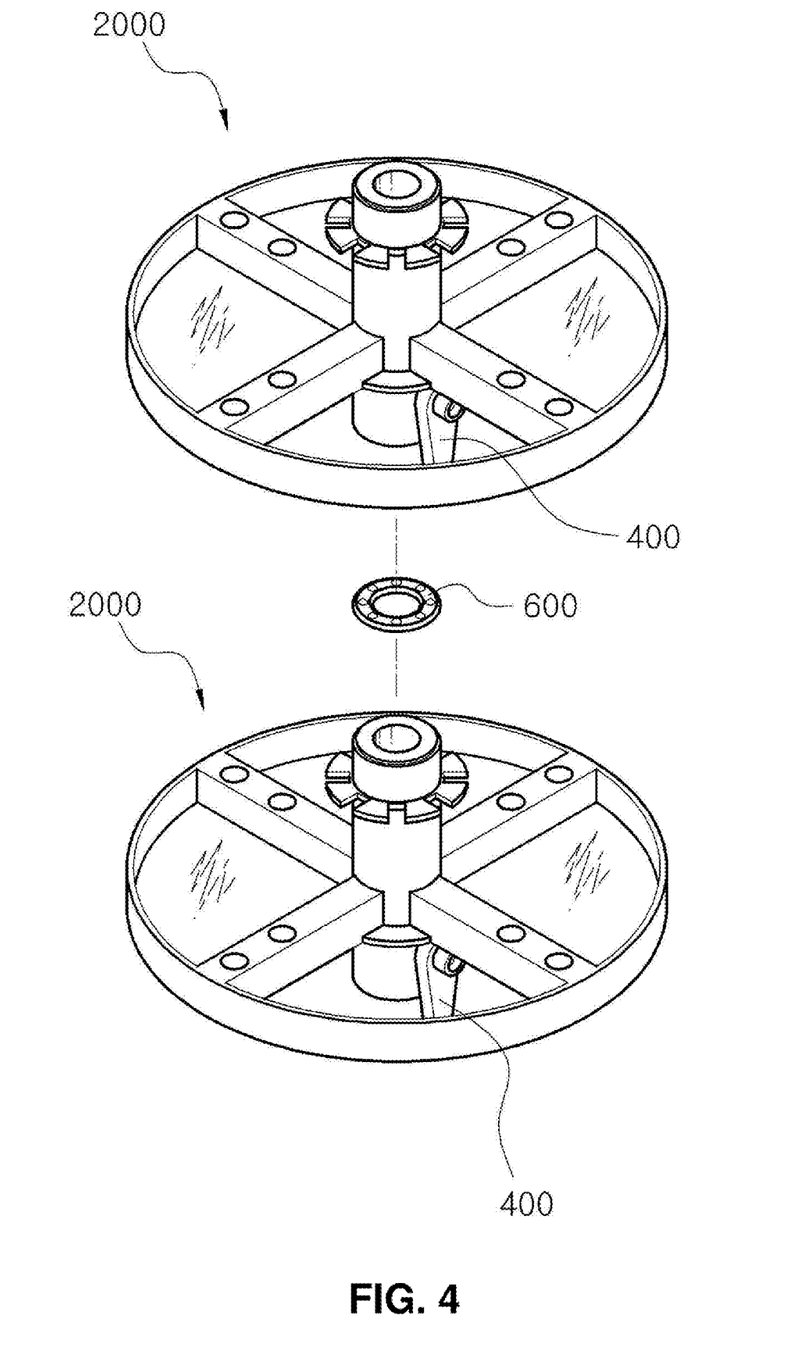
FIG. 4 is an exploded perspective view illustrating a position of a bearing where the plurality of lower rotary units is formed at the sample storage apparatus according to the present invention.

FIG. 4 is an exploded perspective view illustrating a position of a bearing where the plurality of lower rotary units is formed at the sample storage apparatus according to the present invention.

As shown in FIG. 4, where the plurality of lower rotary units 2000 is formed therein, the bearings 600 are formed between lower rotary units 2000.

The bearings 600 serve to smoothly rotate the first and second rotary tables 200 between them.

Also, at least two through holes 310 can be formed at the first and second partition members 300 in a predetermined distance.

Figure 5:
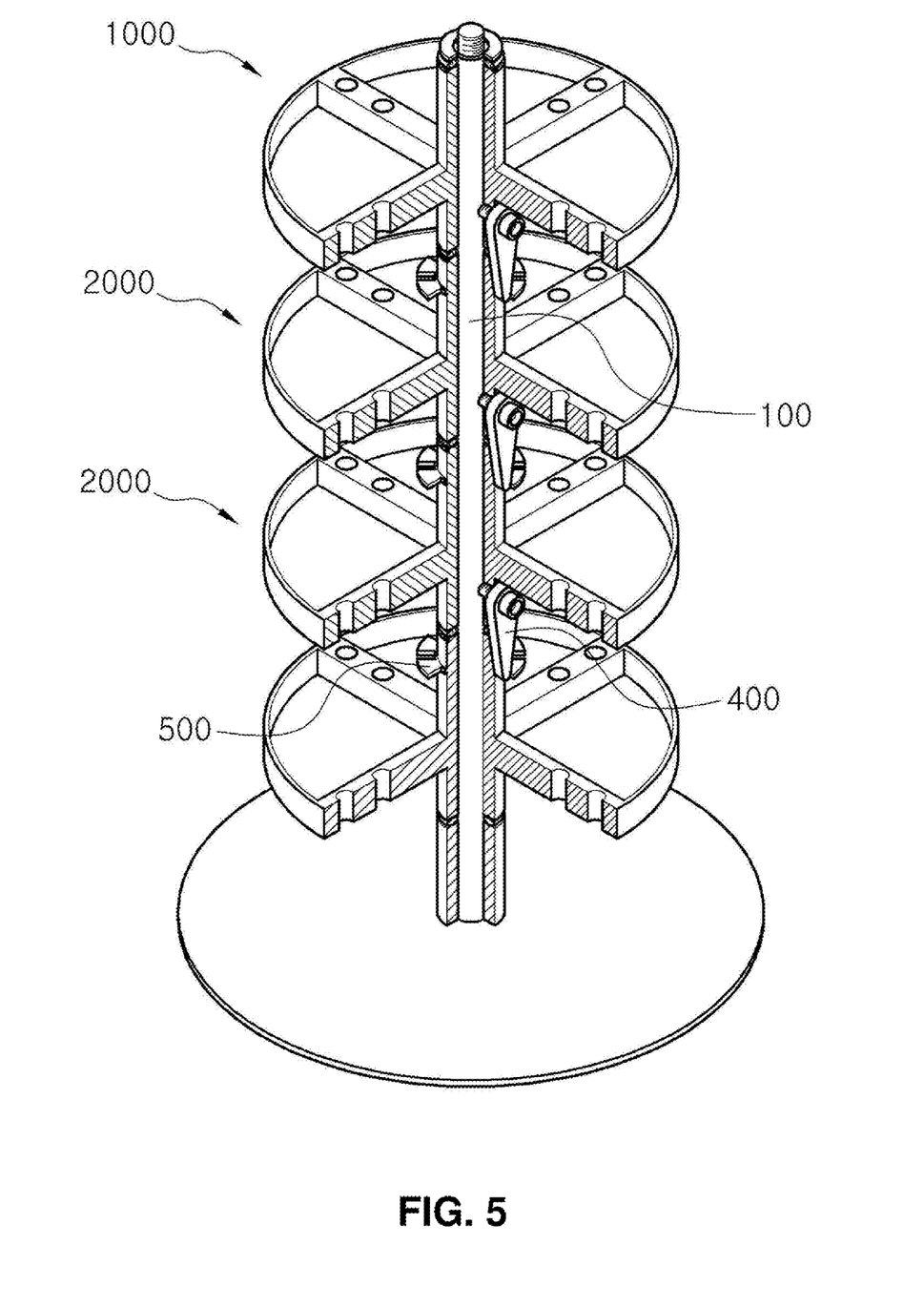
FIG. 5 is a perspective view illustrating the sample storage apparatus according to the present invention in that the rotating axis is coupled to the upper rotary unit and the plurality of lower rotary units.

FIG. 5 is a perspective view illustrating the sample storage apparatus according to the present invention in that the rotating axis is coupled to the upper rotary unit and the plurality of lower rotary units.

Figure 6:
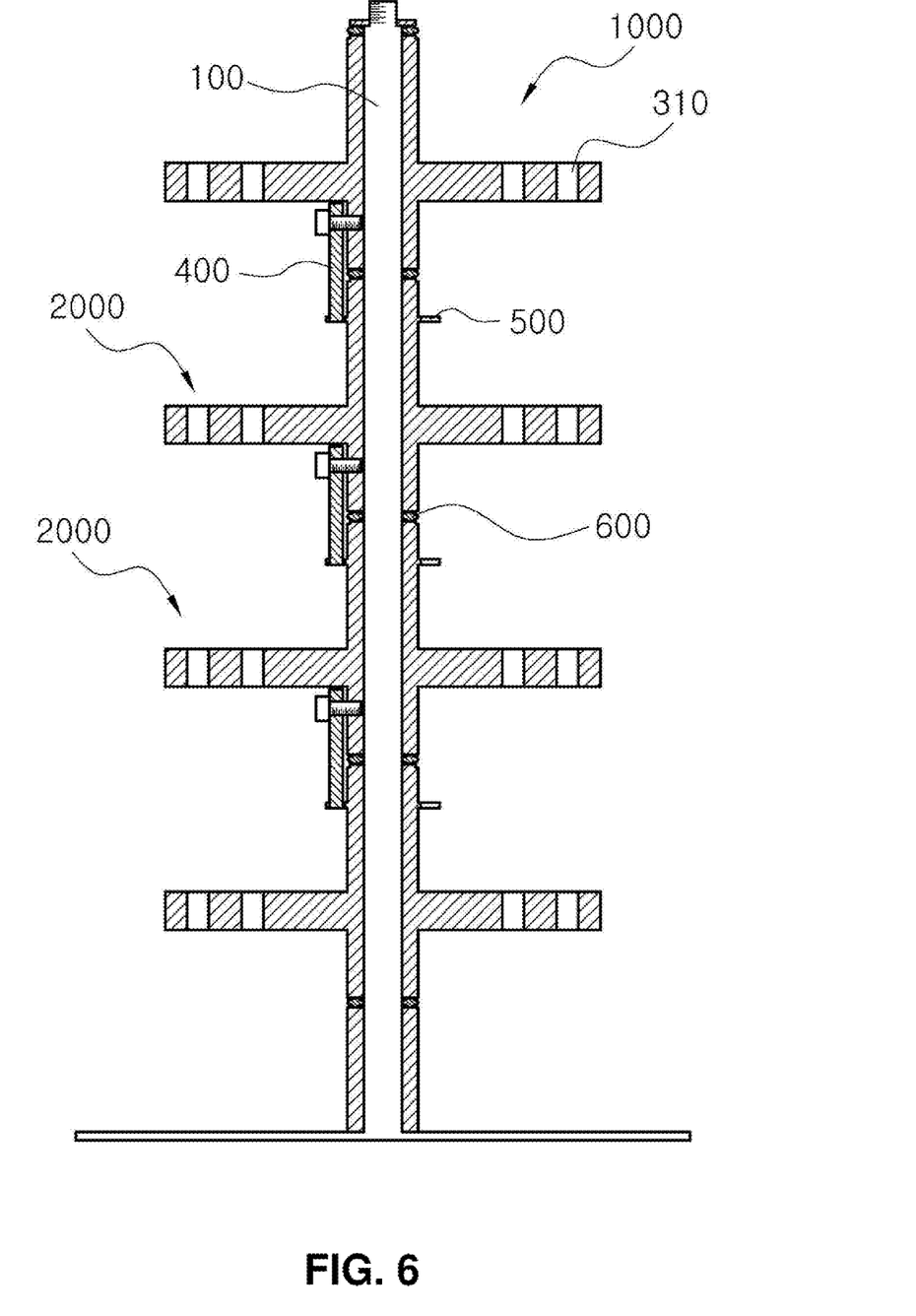
FIG. 6 is a sectional view illustrating the sample storage apparatus according to the present invention in that the rotating axis is coupled to the upper rotary unit and the plurality of lower rotary units.

FIG. 6 is a sectional view illustrating the sample storage apparatus according to the present invention in that the rotating axis is coupled to the upper rotary unit and the plurality of lower rotary units.

As shown in FIG. 5 and FIG. 6, the sample storage apparatus according to the present invention includes a rotating axis 100; an upper rotary unit 1000 having a first rotary table 200 having a first upper cylinder portion 210 protruded upward from an upper middle portion thereof and allowing a rotating axis 100 to be inserted therein and a first lower cylinder portion 220 protruded downward from a lower middle portion thereof and allowing the rotating axis 100 to be inserted therein, at least one first partition members 300 for partitioning off an upper surface of the first rotary table 200 formed at the upper surface of the first rotary table 200, and a first fixing member 400 coupled to one side of an outer circumference of the first lower cylinder portion 220 through a first hinge coupling portion 410 and having a lower portion protruded downward from a lower end of the first lower cylinder portion 220 and a first slanting portion 420 formed at one side of an upper end thereof so as to form a first fixing gap angle 430; and a lower rotary unit 2000 located at a lower portion of the upper rotary unit 1000 having a second rotary table 200 having a second upper cylinder portion 210 protruded upward from an upper middle portion thereof and allowing the rotating axis 100 to be inserted therein and a second lower cylinder portion 220 protruded downward from a lower middle portion thereof and allowing the rotating axis 100 to be inserted therein; at least one second partition members 300 for partitioning off an upper surface of the second rotary table 200 formed at the upper surface of the second rotary table 200, a second fixing member 400 coupled to one side of an outer circumference of the second lower cylinder portion 220 through a second hinge coupling portion 410 and having a lower portion protruded downward from a lower end of the second lower cylinder portion 220 and a second slanting portion 420 formed at one side of an upper end thereof so as to form a second fixing gap angle 430, and a latching member 500 formed along an outer circumference of the second upper cylinder portion 210 and having a plurality of second insertion holes 510 for allowing a lower end of the first fixing member 400 of the upper rotary unit 1000 to be inserted therein.

Here, at least two lower rotary units 2000 are stacked up another.

Also, the second fixing member 400 may be not formed at the lowermost lower rotary unit 2000. The latching member 500 may be not formed at the upper rotary unit 1000.

Figure 7:
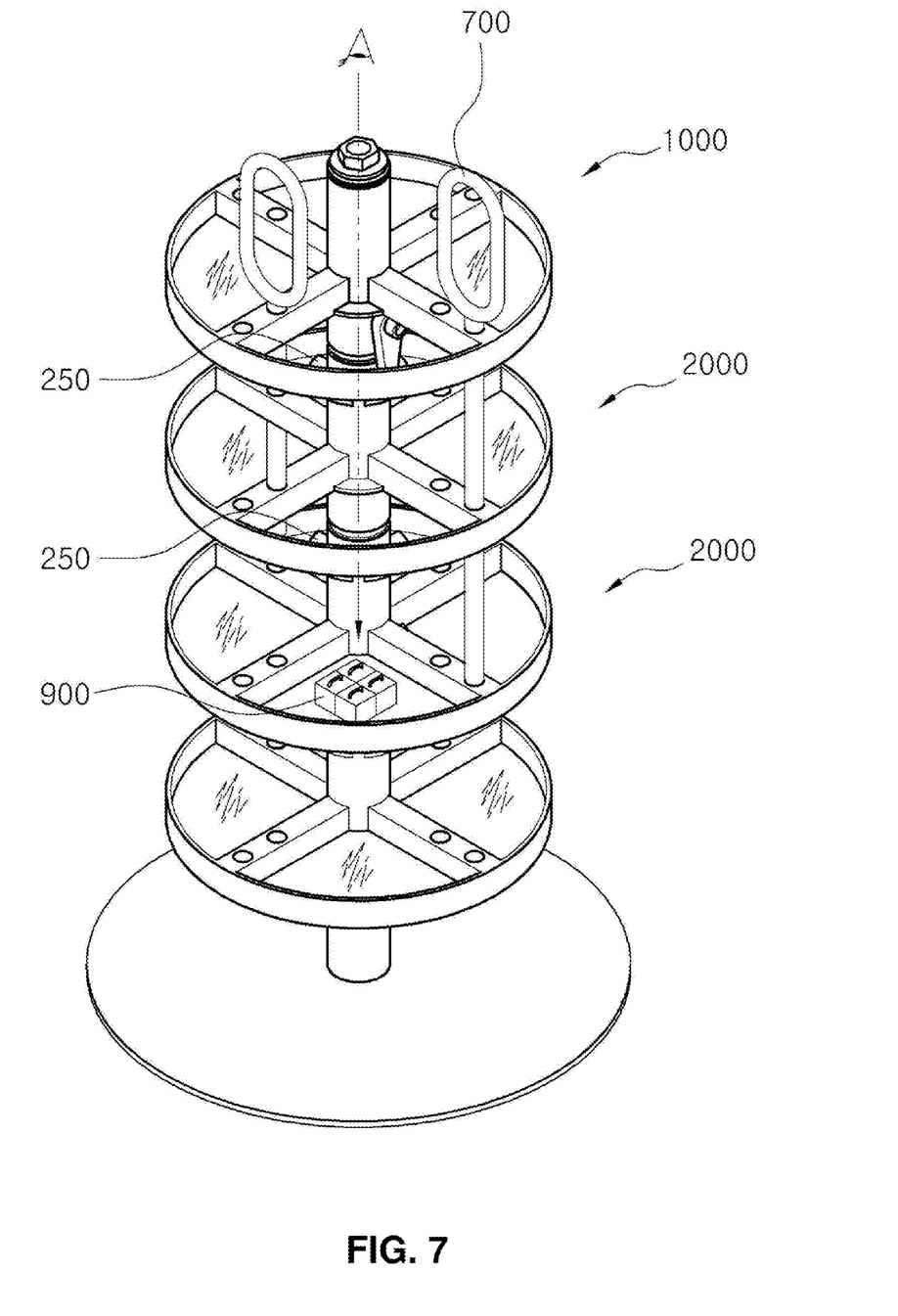
FIG. 7 is an exampling view illustrating incoming and outgoing status of the sample storage box stored in the sample storage apparatus according to the present invention in that the rotating axis is coupled to the upper rotary unit and the plurality of lower rotary units.

FIG. 7 is an exampling view illustrating incoming and outgoing status of the sample storage box stored in the sample storage apparatus according to the present invention in that the rotating axis is coupled to the upper rotary unit and the plurality of lower rotary units.

Figure 8:
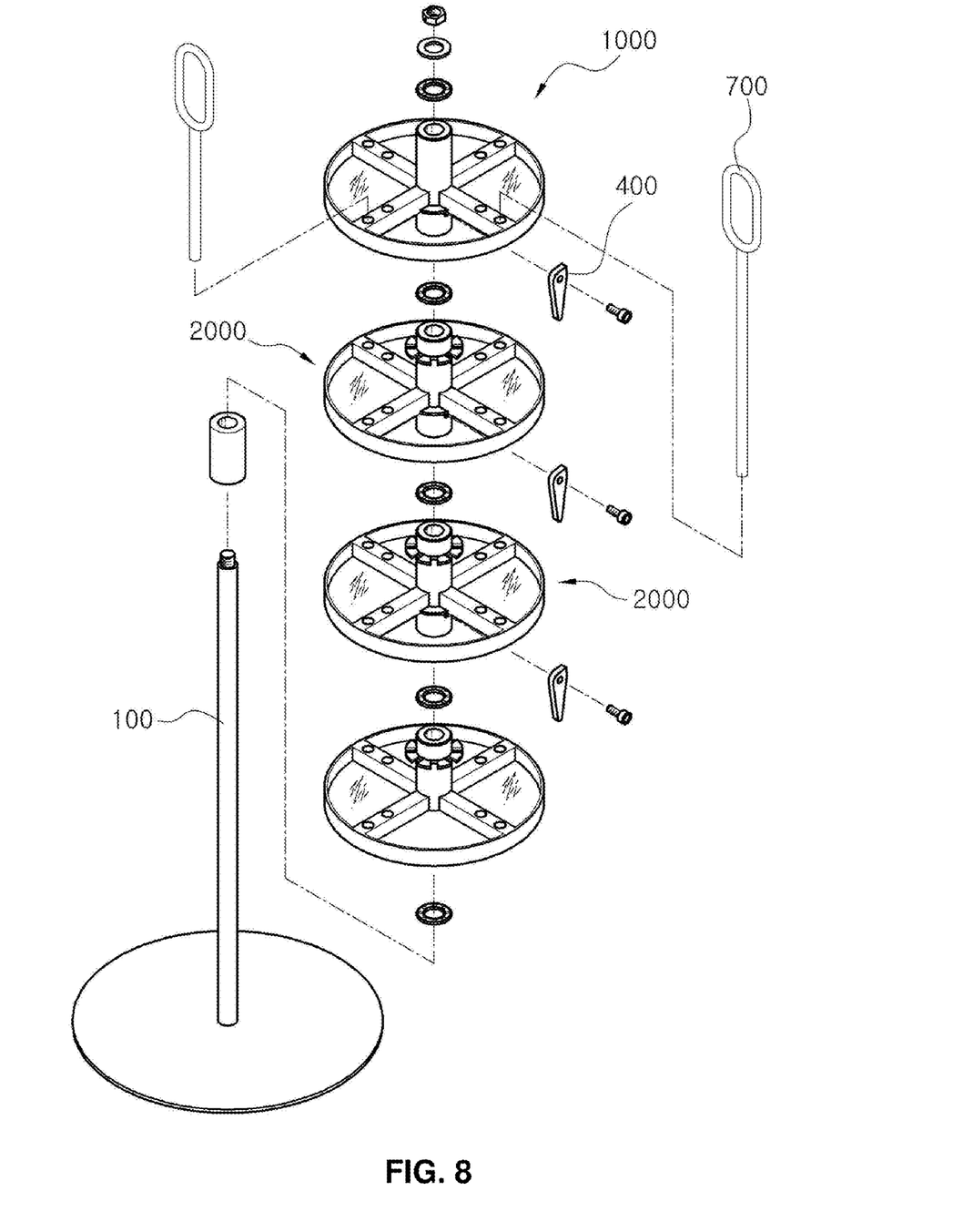
FIG. 8 is an exploded perspective view illustrating the sample storage apparatus according to the present invention in that the rotating axis is coupled to the upper rotary unit and the plurality of lower rotary units.

FIG. 8 is an exploded perspective view illustrating the sample storage apparatus according to the present invention in that the rotating axis is coupled to the upper rotary unit and the plurality of lower rotary units.

As shown in the drawings, the sample storage boxes 900 are located at the third rotary tables 200 from upside thereof.

Here, in order to draw out the sample storage boxes 900 or insert the sample storage boxes 900 therein, any one viewing hole 250 formed on the upper rotary unit 1000 is coincided with another viewing hole 250 formed at the lower rotary unit 2000 located right below the upper rotary unit 1000, so that the operator can look at the sample storage boxes 900 seated on the third rotary tables 200.

The viewing hole 250 can have any angle capable of viewing the sample storage boxes 900 of a predetermined size. Here, it is preferred that the angle of the viewing hole 250 may be 90° through 180°.

Also, where the angle of the viewing hole 250 becomes smaller, the storing area thereof is widened.

However, it is preferred that the maximum space is ensured so as to draw out the sample storage boxes 900 or insert the sample storage boxes 900 therein.

That is, since the viewing hole 250 serves to ensure his view as well as provide the path of the sample storage boxes 900, it is preferred that the size of the viewing hole 250 is larger than the entire size of the sample storage boxes 900.

Accordingly, the angle of the viewing hole 250 may be 0° through 15°, 15° through 30°, 30° through 60°, 60° through 90°, 90° through 180°, or 0° through 45°, 45° through 90°, 90° through 180° etc. according to the variety sizes of the sample storage boxes 900.

Also, as shown in the drawings, fixing poles 700 are inserted into any through holes formed at the partition members 300, so that the upper rotary unit 1000 can be simultaneously rotated with the lower rotary unit 2000 located right above the third lower rotary unit 2000.

Accordingly, the multilayered rotary tables 200 are inserted into the rotating axis 100, so that the plurality of sample storage boxes 900 is stored in the multilayered rotary table, whereby it can effectively and maximally ensure the space for storing the samples.

Figure 9:
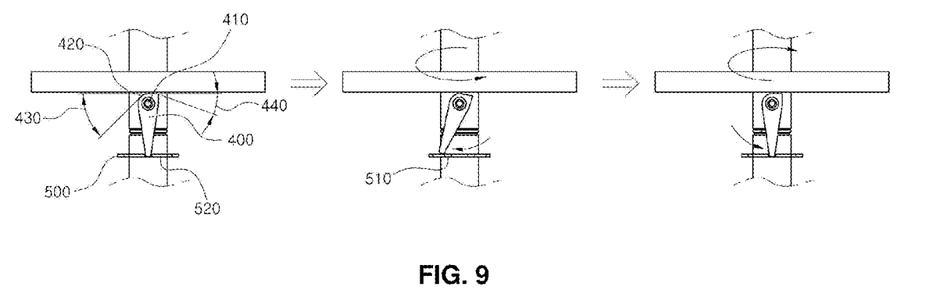
FIG. 9 is an exampling view a status of hanging the fixing member on the latching member of the sample storage apparatus according to the present invention.

FIG. 9 is an exampling view a status of hanging the fixing member on the latching member of the sample storage apparatus according to the present invention.

As shown in FIG. 9, the fixing member 400 is coupled to one side of the outer circumference of the lower cylinder portion 220 through the hinge coupling portion 410. Also, the fixing member includes the lower portion protruded downward from the lower end of the second lower cylinder portion 220 and the slanting portion 420 formed at one side of an upper end thereof so as to form the fixing gap angle 430.

Here, the fixing gap angle 430 means any angle between the fixing member 400 and the rotary table 200 located on the upper portion of the corresponding fixing member 400.

Also, the latching member 500 is formed along the outer circumference of the upper cylinder portion 210. Here, the latching member 500 includes the plurality of second insertion holes 510 for allowing the lower end of the fixing member 400 of the upper rotary unit 1000 or the lower rotary unit 2000 to be inserted therein.

Also, the plurality of the insertion hole 510 is formed between protrusions 520.

Here, since the fixing gap angle 430 is formed, the lower end of the fixing member 400 can go up the upper end of the protrusion 520 during the rotation in any direction thereof. In the meantime, where the fixing member 400 is rotated in the opposite direction, since the lower end of the fixing member 400 is contacted with the side surface of the protrusion 520, the upper rotary table 200 can be rotated together with the lower rotary table 200 located right below the upper rotary table 200.

That is, the upper rotary table 200 can be simultaneously rotated with the lower rotary table 200 located right below the upper rotary table 200 through the fixing member 400 and the latching member 500.

In the meantime, an absorbing angle 440 can be formed at the opposite portion of the fixing gap angle 430.

Here, the absorbing angle 440 is more than 0°. However, the absorbing angle 440 is smaller than the fixing gap angle 430.

As shown in FIG. 9, when the upper rotary table 200 is rotated in the direction of the fixing gap angle 430, the upper rotary table 200 is simultaneously rotated with the lower rotary table 200 located right below the upper rotary table 200. On the contrary, where the upper rotary table 200 is rotated in the opposite direction of the fixing gap angle 430, that is, in the direction of the absorbing angle 440, the upper rotary table 200 is not engaged with the lower rotary table 200, so that the upper rotary table 200 can be freely rotated.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A sample storage apparatus comprising:
a rotating axis;
a rotary table having an upper cylinder portion protruded upward from an upper middle portion thereof and allowing the rotating axis to be inserted therein and a lower cylinder portion protruded downward from a lower middle portion thereof and allowing the rotating axis to be inserted therein;
at least one partition member for partitioning off an upper surface of the rotary table formed at the upper surface of the rotary table;
a fixing member coupled to one side of an outer circumference of the lower cylinder portion through a hinge coupling portion and having a lower portion protruded downward from a lower end of the lower cylinder portion and a slanting portion formed at one side of an upper end thereof so as to form a fixing gap angle; and
a latching member formed along an outer circumference of the upper cylinder portion and having a plurality of insertion holes for allowing a lower end of the fixing member to be inserted therein.

2. A sample storage apparatus as claimed in claim 1, further comprising at least two through holes formed at the partition members in a predetermined distance.

3. A sample storage apparatus as claimed in claim 1, wherein a plurality of rotary tables is stacked up another through the rotating axis.

4. A sample storage apparatus as claimed in claim 3, further comprising a bearing having an axis insertion hole for allowing the rotating axis to be inserted therein located on the upper cylinder portion.

5. A sample storage apparatus as claimed in claim 3, further comprising viewing holes formed at least one partition district of the rotary table divided by the partition members.

6. A sample storage apparatus comprising:
a rotating axis;
an upper rotary unit having a first rotary table having a first upper cylinder portion protruded upward from an upper middle portion thereof and allowing a rotating axis to be inserted therein and a first lower cylinder portion protruded downward from a lower middle portion thereof and allowing the rotating axis to be inserted therein, at least one first partition members for partitioning off an upper surface of the first rotary table formed at the upper surface of the first rotary table, and a first fixing member coupled to one side of an outer circumference of the first lower cylinder portion through a first hinge coupling portion and having a lower portion protruded downward from a lower end of the first lower cylinder portion and a first slanting portion formed at one side of an upper end thereof so as to form a first fixing gap angle; and
a lower rotary unit located at a lower portion of the upper rotary unit having a second rotary table having a second upper cylinder portion protruded upward from an upper middle portion thereof and allowing the rotating axis to be inserted therein and a second lower cylinder portion protruded downward from a lower middle portion thereof and allowing the rotating axis to be inserted therein; at least one second partition members for partitioning off an upper surface of the second rotary table formed at the upper surface of the second rotary table, a second fixing member coupled to one side of an outer circumference of the second lower cylinder portion through a second hinge coupling portion and having a lower portion protruded downward from a lower end of the second lower cylinder portion and a second slanting portion formed at one side of an upper end thereof so as to form a second fixing gap angle, and a latching member formed along an outer circumference of the second upper cylinder portion and having a plurality of insertion holes for allowing a lower end of the first fixing member of the upper rotary unit to be inserted into the insertion holes, wherein at least two lower rotary units are stacked up another.

7. A sample storage apparatus as claimed in claim 6, wherein at least two through holes are formed at the first and second partition members in a predetermined distance.

8. A sample storage apparatus as claimed in claim 7, wherein fixing poles are inserted into any through holes formed at the partition members, whereby at least two rotary tables can be fixed.

9. A sample storage apparatus as claimed in claim 6, further comprising viewing holes formed at least one partition district of the rotary table divided by the partition members.

10. A sample storage apparatus as claimed in claim 6, wherein an upper rotary table is simultaneously rotated with a lower rotary table, when the upper rotary table is rotated in the direction of the fixing gap angle.

11. A sample storage apparatus as claimed in claim 6, wherein where an upper rotary table is rotated in the opposite direction of the fixing gap angle, the upper rotary table is not engaged with a lower rotary table, whereby the upper rotary table can be freely rotated.

12. A sample storage apparatus comprising:
a rotating axis;
an upper rotary unit having a first rotary table having a first upper cylinder portion protruded upward from an upper middle portion thereof and allowing a rotating axis to be inserted therein and a first lower cylinder portion protruded downward from a lower middle portion thereof and allowing the rotating axis to be inserted therein, at least one first partition members for partitioning off an upper surface of the first rotary table formed at the upper surface of the first rotary table, and a first fixing member coupled to one side of an outer circumference of the first lower cylinder portion through a first hinge coupling portion and having a lower portion protruded downward from a lower end of the first lower cylinder portion and a first slanting portion formed at one side of an upper end thereof so as to form a first fixing gap angle; and
a lower rotary unit located at a lower portion of the upper rotary unit having a second rotary table having a second upper cylinder portion protruded upward from an upper middle portion thereof and allowing the rotating axis to be inserted therein and a second lower cylinder portion protruded downward from a lower middle portion thereof and allowing the rotating axis to be inserted therein; at least one second partition members for partitioning off an upper surface of the second rotary table formed at the upper surface of the second rotary table, a second fixing member coupled to one side of an outer circumference of the second lower cylinder portion through a second hinge coupling portion and having a lower portion protruded downward from a lower end of the second lower cylinder portion and a second slanting portion formed at one side of an upper end thereof so as to form a second fixing gap angle, and a latching member formed along an outer circumference of the second upper cylinder portion and having a plurality of insertion holes for allowing a lower end of the first fixing member of the upper rotary unit to be inserted into the insertion holes, wherein at least two lower rotary units are stacked up another, and a bearing having an axis insertion hole for allowing the rotating axis to be inserted therein located on the second upper cylinder portion is formed between the upper and lower rotary units or between the lower rotary units, where the plurality of lower rotary units is formed therein.

* * * * *